United States Patent [19]

Imura

[11] 4,157,708

[45] Jun. 12, 1979

[54] EYE FUNDUS PLETHYSMOGRAPH ASSEMBLY

[75] Inventor: Kenji Imura, Osaka, Japan

[73] Assignee: Minolta Camera Kabushiki Kaisha, Osaka, Japan

[21] Appl. No.: 734,768

[22] Filed: Oct. 22, 1976

[30] Foreign Application Priority Data

Oct. 29, 1975 [JP] Japan .................... 50/130651

[51] Int. Cl.² ......................... A61B 5/02
[52] U.S. Cl. .................................. 128/666
[58] Field of Search ............... 128/2 L, 2 T, 2.05 F, 128/2.05 V, 2.05 P; 73/79, 80; 351/6, 7, 8, 9; 356/39–41

[56] References Cited

U.S. PATENT DOCUMENTS

| | | | |
|---|---|---|---|
| 2,640,389 | 6/1953 | Liston | 128/2 L |
| 3,572,100 | 5/1969 | Grolman et al. | 73/80 |
| 3,647,299 | 3/1972 | Lavalee | 128/2 L |
| 3,677,648 | 7/1972 | Dorsch | 128/2.05 F |
| 3,679,295 | 7/1972 | Newman et al. | 351/6 |
| 3,811,777 | 5/1974 | Chance | 128/2 L |
| 3,814,081 | 6/1974 | Mori | 128/2 L |
| 3,822,695 | 7/1974 | Takayama | 128/2 L |
| 3,825,342 | 7/1974 | Lubbers et al. | 128/2 L |
| 3,847,483 | 11/1974 | Shaw et al. | 128/2 L |
| 3,893,447 | 7/1975 | Hochheimer et al. | 128/2 T |
| 3,948,248 | 4/1976 | Zuckerman et al. | 128/2 T |
| 3,998,550 | 12/1976 | Konishi et al. | 128/2 L |

FOREIGN PATENT DOCUMENTS

| | | | |
|---|---|---|---|
| 656074 | 1/1963 | Canada | 356/41 |
| 4952395 | 5/1974 | China | 128/2 T |

OTHER PUBLICATIONS

"The Choroidal Eye Oximeter: Instrument for $Q_2$ Saturation Meas. In Vivo", Laing, R.A. et al., IEEE Trans on Biomed Engr., vol. 22, #3 5/75, pp. 183–195.
"ALED Skin Reflectance Oximeter", Cohen, A. et al., Med. & Biol. Engrg., vol. 10, #3, 1972, pp. 385–391.
"Multiple Scattering Analysis of Retinal Blood Oximetry", Cohen, A. et al., IEEE Trans. on Biomed Engrg., vol. 23, #5, pp. 391–400, Sep. '76.
"Photoelectric Method of Investigating Amount of Blood in Fundus Ocul", Broadfoot, K. D. et al., Brit. Jrnl. Ophthal. (1961, vol. 45), pp. 161–182.

*Primary Examiner*—Robert W. Michell
*Assistant Examiner*—Francis J. Jaworski
*Attorney, Agent, or Firm*—Harold L. Jackson; Stanley R. Jones; Joseph W. Price

[57] ABSTRACT

An eye fundus plethysmograph assembly is provided for determining variations in the amount of blood present at the fundus of the eye. A source of at least a first and second wavelength of light energy is specifically directed into a subject eye for reflection from the retina or fundus of the eye. The reflected light is directed at a receiving element that can produce a first output signal representative of a reflected first wavelength and a second output signal representative of a reflected second wavelength. A processing circuit is provided for subtracting one of the first and second output signals from the other to provide a representative measurement output of the amount of blood in the blood vessels adjacent the eye fundus. The output signals can be recorded or displayed in any desired form to facilitate the interpretation of the amount of blood present.

13 Claims, 5 Drawing Figures

EYE FUNDUS PLETHYSMOGRAPH ASSEMBLY

BACKGROUND OF THE INVENTION

1. Field of the Invention

The present invention relates to a measurement instrument in the field of medical electronics. More particularly to a plethysmograph for determining and registering variations in the size of an organ or limb and in the amount of blood present or passing through it.

2. Description of the Prior Art

The use of plethysmograph instruments in the medical field has been known for a considerable period of time. Generally, light rays are transmitted into a finger or earlobe of the human body. An output signal is derived from either the light rays transmitted through or reflected off the body. The resulting plethysmogram is a plot showing a train of waves representative of the amount of blood present in that region of the human body.

Reference is made to the article, "Photoelectric Determination of Arterial Oxygen Saturation in Man", by Wood et al in the Journal of Laboratory and Clinical Medicine, Vol. 34, 1949. In that article, an oximeter is described wherein a light source generates light in the infrared region and in the red region. Light wave signals that are transmitted through the pinna of the human ear are photoelectrically converted into a first and second output signal to determine the oxygen saturation in the arterial blood. The Herczfeld et al U.S. Pat. No. 3,704,706 discloses an apparatus for the detection of pulse repetition rate and oxygenation of blood flow by the direction of light through a patient's finger. Additional examples of prior art can be found in the Liston U.S. Pat. No. 2,640,389 and the Polanyi et al U.S. Pat. No. 3,628,525.

Common problems have existed in the subjective calibration of the instruments to a particular patient and the sensitivity of the instruments to various conditions of the skin. One of the more important regions of the human body to monitor the normality of blood flow relates to the brain, since serious damage is capable of happening in a relative short period of time. Thus, the prior art is still seeking improvements in plethysmograph devices.

SUMMARY OF THE INVENTION

The present invention is an advancement in the field of medical science, in that it provides a novel plethysmograph assembly for obtaining a plethysmogram from a region of the human body in which a plethysmograph has not previously been obtained. The present invention provides an eye fundus plethysmograph assembly which includes a source of at least a first and second wavelength of light energy. Means are provided for directing a beam of light energy from the source into a subject eye. Photoreceptive means are provided for receiving a reflective portion of the beam of light energy from the fundus of the subject eye. The photoreceptive means provides a first output signal representative of the reflective first wavelength and a second output signal representative of the reflected second wavelength. These output signals are processed by a circuit means which subtracts one of the first and second output signals from the other to provide a representative measurement output of the amount of blood in the blood vessels adjacent the eye fundus. The resultant plethysmogram provides a unique monitoring characteristic of the eye that heretofore has not been available to the medical profession. It is expected that a diagnosis of various abnormalities of the body such a diabetes and arteriosclerosis can be ascertained from this plethysmogram. Additionally the eye fundus plethysmograph will permit a close monitoring of the blood flow to the brain. Finally, the eye fundus plethysmograph assembly can be integrated with eye fundus photography to permit a unique diagnosis of the subject patient. The present invention provides not only a unique eye fundus plethysmograph assembly, but also the recognition of the unique problems associated with obtaining a plethysmogram from the fundus of an eye.

The features of the present invention which are believed to be novel are set forth with particularity in the appended claims. The present invention, both as to its organization and manner of operation, together with further objects and advantages thereof, may best be understood by reference to the following description, taken in connection with the accompanying drawings.

DESCRIPTION OF THE PREFERRED EMBODIMENTS

Figure 1:
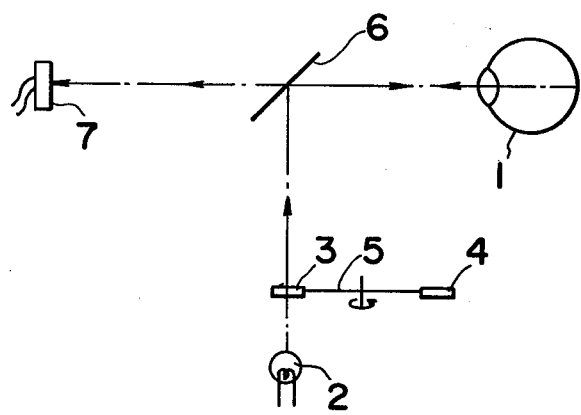
FIG. 1 is a schematic cross-sectional view of the optical design of a first embodiment of the present invention.

The following specification taken in conjunction with the drawings, sets forth the preferred embodiments of the present invention in such a manner that any person skilled in the optical and medical field can utilize the invention. The embodiments of the invention disclosed herein, are the best modes contemplated by the inventor in carrying out his invention in a commercial environment, although it should be understood that various modifications can be accomplished within the parameters of this invention.

As can be appreciated, the eye is enclosed by three membranes. The upper most one consists of the transparent cornea, forming the bulge, and the opaque sclera, enclosing the remainder of the eyeball. The choroid coat, contains many nerves and blood vessels and is immediately under the sclera. The innermost membrane of the eye is the retina which lines all of the posterior wall or fundus. Behind the cornea is the iris in the lens. Muscles in the eye change the size of the pupil for opening of the lens and other muscles change the shape of the crystalline lens. Two chambers, one interior to the lens and the other posterior are filled with transparent material. The first with the aqueous humor and the second with the vitreous humor. The aqueous humor has a water consistency similar to blood plasma and the vitreous humor is jellylike. Although the retina includes blood vessels, the major blood supply of the eye is the choroid coat.

As can be appreciated, major refraction occurs at the cornea because this is the largest refracted index change resulting from the index of air to the index of the medium of the cornea. Generally, the cornea will absorb light of all wavelengths shorter than about 320 nanometers and since the ocular medium is essentially water, it will absorb most wavelengths longer than 1400 nanometers. As can be appreciated, the surface of the cornea and the transmission of the ocular medium will vary in a subjective manner with each patient. For example, blue light will be attenuated heavily particularly in older eyes because of the absorption and scattering in the crystalline lenses.

Thus, the light rays that are reflected from the eye will include not only the desired light rays reflected off of the fundus, but also light rays which have not entered into the eyeball but have been reflected directly by the surface of the cornea of the eye. In addition, the eye itself is constantly seeking to accommodate the ambient light and the eyeball will tremble in minute movements even if a patient is apparently steadily looking at a point object. This minute trembling of the eyeball will further result in irregular variations in the light rays which are reflected directly from the cornea to produce a resultant disturbing noise in the reflected light signal.

In accordance with the present invention, it has been discovered that a pair of light rays of a predetermined wavelength both experience substantially identical reflecting power characteristic from the cornea while the relecting light rays from the fundus representative of the presence of blood in the blood vessels will show a difference in reflectance depending upon the wavelength of the light.

Basically the measurement of the plethysmogram from the fundus of an eye involves the direction of light rays into the eyeball with a measurement of the reflected light from the fundus providing the measurement signals. The intensity of the reflected light from the fundus will vary due to a pulsation of blood through the blood vessels distributed throughout the fundus such as in the choroid coat. This variation or alternating current component can be recorded as a plethysmogram.

The incident light can be assumed to have an intensity of $I_0$. The relative transmittance of light from the ambient air medium through the aqueous humor and the vitreous humor to the fundus of the eyeball can be assumed to be a constant transmittance of A. The light absorption coefficient of the blood layer at the fundus is K, while the thickness of the blood layer, which will vary with time, can be given as $x(t)$. The reflecting power of the visual rod and cone receptors and layers of the fundus of the eyeball is R. Finally, the transmittance of the reflected light rays from the fundus to the outside of the eyeball is B. If the same optical path is traversed as the incident light, then theoretically the transmittance B would equal A.

As can be appreciated, the thickness of the blood layer $x(t)$ is a function of time due to the resiliency of the blood vessel and the pulsation from the heartbeat. Thus, the intensity, $S_1$ of reflected light from the fundus of the eyeball is given as follows;

$$S_1 = I_0 \cdot A \cdot e^{-K \cdot x(t)} \cdot R \cdot B \quad (1)$$

This measurable reflected light from a subject's eyeball will contain not only the reflected light from the fundus of the eyeball, but also the light which is directly reflected from the surface of the cornea. If we assume a reflecting power, C, of the cornea, then the intensity, $S_2$, of reflected light from the surface of the cornea can be given as follows;

$$S_2 = I_0 \cdot C \quad (2)$$

Accordingly, the equation for the total reflected light $\overline{S}$, which can be measured from the eyeball is given as follows;

$$\overline{S} = S_1 + S_2 = I_0 \cdot A \cdot e^{-K \cdot x(t)} \cdot R \cdot B + I_0 \cdot C \quad (3)$$

It has been discovered that the eyeball during a measurement period will undergo minute movements in attempting to accommodate and perform its physiological function even when the subject to told to keep a specific target in sight. These minute movements of the eyeball are generally in the order of 30 to 100 Hz and frequently peak at 50 Hz. In considering the influence of the aforesaid minute movements in the resulting light intensity measured, it is possible to regard the factors A, R, and B as constants irrespective of the aforesaid minute movements of the eyeball. The reflecting power, C, of the cornea, however will vary because the angle of the reflecting surface varies in correlation with the minute movements of the eyeball. Accordingly, the light intensity which is measured will also vary with a resulting noise factor and the measured signal must be compensated. It has been discovered in the present invention that incident light having two different wave lengths $\lambda_1$ and $\lambda_2$ can be used to solve this noise factor problem. Accordingly it is possible to redraft equation 3 as follows;

$$S\lambda_1 = I_0\lambda_1 \cdot A\lambda_1 \cdot e^{-K\lambda_1 \cdot x(t)} \cdot R\lambda_1 \cdot B\lambda_1 + I_0\lambda_1 \cdot C\lambda_1$$

$$S\lambda_2 = I_0\lambda_2 \cdot A\lambda_2 \cdot e^{-K\lambda_2 \cdot x(t)} \cdot R\lambda_2 \cdot B\lambda_2 + I_0\lambda_2 \cdot C\lambda_2$$

(4)

In the above equations, the factors $R\lambda_1$, $R\lambda_2$ and $K\lambda_1$, $K\lambda_2$ relate to the characteristics of the fundus and will vary with the wavelengths, while the transmittance $A\lambda_1$, $A\lambda_2$, $B\lambda_1$, $B\lambda_2$, and the reflecting power $C\lambda_1$, and $C\lambda_2$ are primarily depended on the index of refraction of the fluid mediums and within the wavelength range which is transmitted, they may be regarded as constant for each preselected wavelength. Thus, in accordance with the above equations, the following relationships may be given;

$$A\lambda_1 = A\lambda_2 = A, \ B\lambda_1 = B\lambda^2 = B, \ C\lambda_1 = C\lambda_2 = C \quad (5)$$

Accordingly, when the base lines or reference levels for the measurements of $S\lambda_1$ and $S\lambda_2$ are brought into coincidence to obtain a difference (that is a relationship corresponding to $I_0\lambda 1 = I_0\lambda 2 = I_0$) then;

$$S\lambda_1 - S\lambda_2 = I_0 \cdot A \cdot B(R\lambda_1 \cdot e^{-K\lambda_1 \cdot x(t)} - R\lambda_2 \cdot e^{-K\lambda_2 \cdot x(t)}) \quad (6)$$

As is apparent, from the above equation 6, the resulting influence or effect of the reflecting power, C, of the cornea is eliminated. In addition, the following relationships are found that are relevant to equation 6;

$$K\lambda_1 \cdot x(t) << 1 \quad (7)$$

$$K\lambda_2 \cdot x(t) << 1$$

Accordingly, taking these relationships (equations 7) into account, equation 6 can be modified as follows;

$$\bar{S} = I_0 \cdot A \cdot B\{R\lambda_1(1 - K\lambda_1 \cdot x(t)) - R\lambda_2(1 - K\lambda_2 \cdot x(t))\} \quad (8)$$

$$\bar{S} = I_0 \cdot A \cdot B(R\lambda_1 - R\lambda_2)$$
$$+ I_0 \cdot A \cdot B(R\lambda_2 \cdot K\lambda_2 - R\lambda_1 \cdot K\lambda_1) \cdot x(t)$$

As can be appreciated in the equation (8), $I_0$, A, B, $R\lambda_1$, $R\lambda_2$, $K\lambda_1$, and $K\lambda_2$ are constants. Accordingly as can be seen from equation 8 the only variable factor will be the thickness of the blood layer which will vary with time and accordingly a linear function equation has been derived. Thus, it is discovered that by a simple subtraction process, that is $S\lambda_1 - S\lambda_2$, it is possible to provide an output signal, $\bar{S}$, which represents a plethysmogram. With this subtraction process, the influence of any light reflected off of the cornea that would produce resultant noise due to the minute movements in the eyeball is effectively eliminated.

Referring specifically to FIG. 1, the optical apparatus or design of the first embodiment of the present invention is disclosed. A patient's eyeball, 1, is disclosed schematically receiving light rays from a light source 2 emitting the light across a wide range of wavelengths. A synchronized light chopper 5, interposes filters 3 and 4 into the light path. The color filters 3 and 4 provide wavelengths $\lambda_1$ and $\lambda_2$ respectively. A reflective surface or mirror 6 directs the light rays into the eyeball 1. The rotational rate of the light chopper 5 is sufficiently high as compared with the cycle of minute movements of an eyeball so that the eyeball may be regarded as being in a fixed position with respect to successive light rays having the alternate wavelengths $\lambda_1$ and $\lambda_2$. Additionally, noise introduced by eyeball movement is reduced. The light reflected from the eyeball 1 is passed through the half-mirror 6 to be received by a light receptive element or a photodetector 7.

Generally, one of the wavelengths of light is selected to be somewhat longer than the red zone that is about 600 nanometer while another of the light waves is selected to be somewhat shorter than the red zone. By this predetermined selection of the wavelengths, the blood present in the blood vessels of the fundus will show a lesser light absorption for the light $\lambda_1$ of a relatively longer wavelength than for the light $\lambda_2$ of a relatively shorter wavelength. The measured difference in absorption between the two wavelengths can provide the information for determining the amount of blood in the fundus. As can be appreciated, the position of the light chopper 5 and filters 3 and 4 can be varied without affecting the design parameters of the present invention. For example, the light chopper 5 and filters can be positioned immediately upstream of the light receiving element 7.

Figure 2:
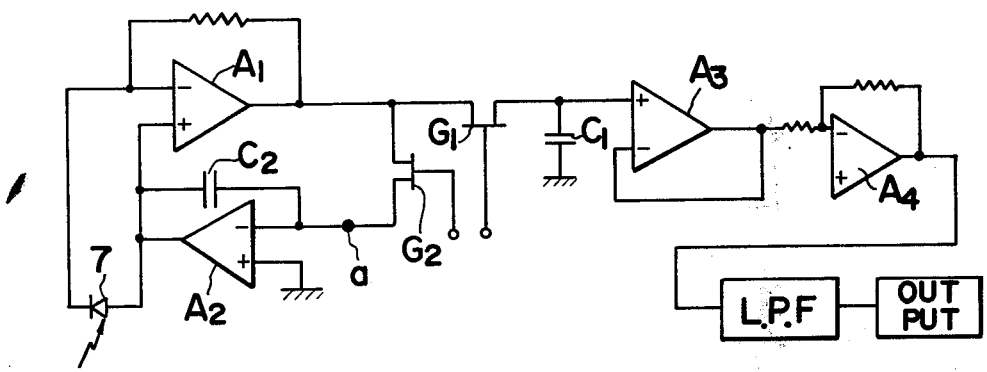
FIG. 2 is a circuit diagram for the first embodiment.

Connected to the photodetector or light receiving element 7, is a timing and signal processing circuit means shown in detail in FIG. 2. The light receiving element 7 consists of a photodiode of a conventional construction, which generates a signal proportional to the magnitude of the incident light energy. A differential amplifier $A_1$ provides a measurement output signal voltage. The respective field effect transistor (FET) $G_1$ and $G_2$ are adapted to be alternately opened in response to the position of the filters 3 and 4 and synchronous with the motor (not shown) of the light chopper 5. As the filter holder or light chopper 5 rotates, a sampling pulse is generated as the light rays intersects substantially the center of each filter. Such a sampling pulse train can be established from the rotation of the driving synchronous motor in a well-known manner; for example employing phased locked loop techniques. These sampling pulses can be applied to the gates in a well-known manner such as shown in U.S. Pat. No. 3,892,490.

Accordingly, the FET gate $G_1$, is conductive when the light of a wavelength $\lambda_1$ is incident on the light receiving photoelectric diode 7. At that time, the condensor $C_1$ will be charged through the gate $G_1$ commensurate with the output of the differential amplifier $A_1$. When the FET gate $G_1$ is rendered nonconductive in response to the rotation of the light chopper 5, the output voltage produced by the amplifier $A_1$ during the $\lambda_1$ interval will be stored on the condensor C1. The buffer amplifier $A_3$ maintains the value of the condensor $C_1$ constant, until the gate $G_1$ is again opened. Because the gate transistor $G_2$ is rendered conductive while the gate $G_1$ is closed, the output of the photoelectric diode 7 representing the light energy of wavelength $\lambda_2$ will charge the condensor $C_2$. When the gate $G_2$ is nonconductive, the voltage value representative of the wavelength $\lambda_2$ energy is stored on the condensor $C_2$. An appropriate buffer amplifier $A_2$ maintains the value of the voltage on the capacitor $C_2$.

With the condensor $C_1$ and $C_2$ now charged, the apparatus is ready to perform a subtraction operation during the next sampling interval. The next sample of light energy of wavelength $\lambda_1$ incident on the light receiving element 7 is sampled and applied to the differential amplifier $A_1$ together with voltage across the capacitor $C_2$. Subtraction is thereby performed between the voltage output of the photoelectric diode 7 representing the light energy of wavelength $\lambda_1$, and the stored voltage of the condensor $C_2$ representative of the light energy of wavelength $\lambda_2$.

The difference, $E\lambda_1 - E\lambda_2$ represents the amount of energy absorbed, and accordingly the amount of blood in the fundus. The differential voltage developed by the differential amplifier and representing $E\lambda_1 - E\lambda_2$ is stored on the capacitor $C_1$, when the gate $G_1$ is activated by a sample signal during the $\lambda_1$ filter interval. When the gate $G_2$ is again activated by a sample signal, condensor $C_2$ will be recharged with an output voltage associated with a new input of the light energy of wavelength $\lambda_2$. Thus, a difference in output voltages obtained due to light signals representative of the energy of respective wavelengths $\lambda_1$ and $\lambda_2$ continually fed to the condensor $C_1$ through the differential amplifier $A_1$ and the gate $G_1$ in the manner described above. The output voltage of the condensor $C_1$ is amplified by way of the buffer amplifier $A_3$ to improve the signal quality of the output signal for additional amplification by the buffer $A_4$. A low pass filter circuit (LPF) can be utilized to remove noise. These circuits are presented only as an example, other circuits equivalent in function are seen as well within the purview of a person of ordinary skill in the art. The elements of these circuits, such as the operational amplifiers, diodes, capacitors and switching transistors are well-known and understood in the prior art. The particular revolutions per minute of the light chopper 5 are determined in accordance with a well-known sampling theorem.

As will be appreciated by those skilled in the art, the voltage on the capacitor $C_2$ should be of the same order of magnitude as that produced by the photodiode in response to a $\lambda_1$ energy signal in order to establish a meaningful difference signal. While not shown specifically, but fully known in the prior art, an attenuation or automatic gain control circuit may be inserted into the circuit at point 'a' to adjust the magnitude of the voltage on capacitor $C_2$ to within the desired reference range. Alternately a band pass filter may be inserted upstream of the light receiving photoelectric diode 7 to limit the light energy transmission band to the desired wavelength range.

Figure 3:
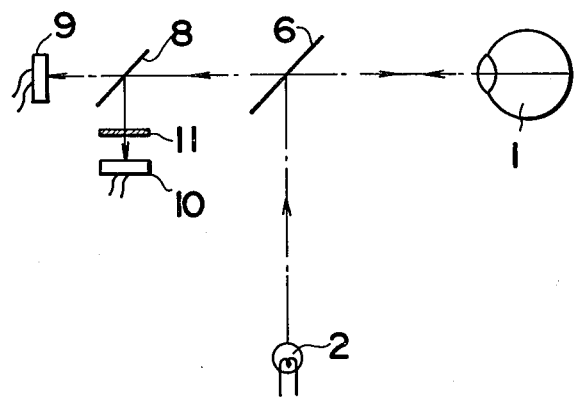
FIG. 3 is a schematical cross-sectional view of the optical design of the second embodiment of the present invention.

Referring to the schematic of FIG. 3, a second embodiment of the optical design features of the present invention is disclosed. In this embodiment, the light rays from the light source 2 of a relative wide bandwidth are reflected on a half-mirror 6 into the eyeball 1. The light reflected from the eyeball 1, including both the light reflected from the fundus and the light reflected from the cornea is transmitted through the half-mirror 6 and then separated by a dichroic mirror 8 into a pair of light rays having respective wavelengths $\lambda_1$ and $\lambda_2$. The photoelectric diodes or light receiving elements 9 and 10 receive the respective light wavelengths $\lambda_1$ and $\lambda_2$ and convert these into electrical signals. As known in the prior art, filter elements can be interposed in front of the light receiving elements 9 and 10 if spectral sensitivity is to be maximized. Mounted within the light path of $\lambda_2$ is an ND (neutral density) filter 11 adapted to adjust the intensity of the incident light on the light receiving photoelectric diode 10 to thereby bring the reference levels or base line of the $\lambda_1$ and $\lambda_2$ signals into coincidence with each other for subtractive processing of their output signals. The ND filter 11 is preferably a variable density filter such as a shiftable wedge-shaped filter. The density of the ND filter is recommended to be adjusted with respect to each individual patient by consulting with an oscillograph displaying the $\lambda_1$ and $\lambda_2$ signals.

Figure 4:
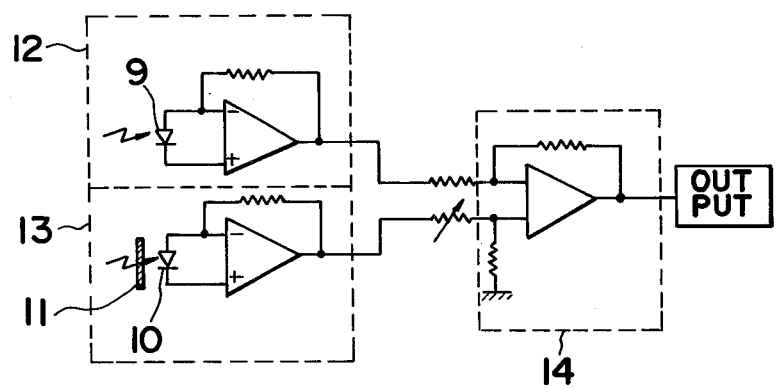
FIG. 4 is a circuit diagram of the second embodiment.

An appropriate signal processing circuit for the second embodiment is disclosed in FIG. 4. Light receiving and amplifying circuits are disclosed in the boxes 12 and 13. The respective outputs of these light receiving circuits can be detected and compared in a differential amplifying circuit 14. Again the elements of these circuits such as the operational amplifiers, and switching transistors are well-known and understood. As can be appreciated from the illustration, a straight forward signal processing can be utilized as a result of an initial balancing of the reference level between the two representative wavelength signals prior to their application to the photoelectric diodes.

Figure 5:
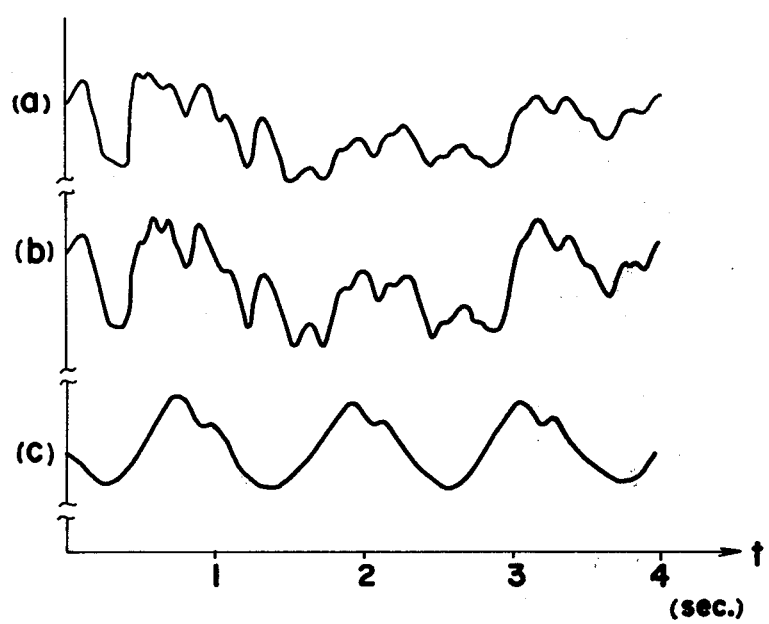
FIG. 5 is graphical plots of the first output, second output and the final plethysmogram obtained by the present invention.

FIG. 5 discloses a graph plotting the results of measurements given in accordance with the present invention. The respective intensity versus time plots designated (a) and (b) are representative of the output signal of the wavelength $\lambda_2$ and the output signal of the wavelength $\lambda_1$. These respective outputs disclose the noise arising from the minute movements of the eyeball so that the determination of any usable waveform is difficult. As noted the abscissa represents time plotted versus intensity. However, since the instantaneous noise is constant, the output (c) resulting from the subtraction process between the outputs (a) and (b), effectively removes the noise to provide a useful plethysmogram.

As can be appreciated by a person skilled in the art, variations of the circuits disclosed are possible by a person skilled in the art.

What is claimed is:

1. An eye fundus plethysmograph assembly capable of measuring the amount of blood in blood vessels adjacent the eye fundus without contacting or distorting the eye comprising;
   means for directing at least a respective first and second wavelength of energy from a source into a subject eye that is physically in a natural undisturbed configuration;
   means for receiving a reflected portion of the respective first and second wavelengths of light energy from the fundus of the subject eye;
   means for producing a first output signal representative of the reflected first wavelength including both a first indication of the blood volume of the eye fundus and a first reflection from the cornea and a second output signal representative of the reflected second wavelength including a second reflection from the cornea, both output signals being produced without altering the natural shape of the subject eye; and
   means for attenuating the respective first and second output signals to a common reference level;
   means for compensating for the cornea reflection by subtracting one of the first and second output signals from the other to provide a representative plethysmograph output of the amount of blood in vessels adjacent the eye fundus over at least a cyclic period of measurement independent of the reflection from the cornea.

2. The invention of claim 1 wherein the first wavelength is longer than 600 nanometers and the second wavelength is shorter than 600 nanometers.

3. The invention of claim 1 further including means for coinciding the base line of variation of the first output signal with the base line of variation of the second output signal.

4. The invention of claim 3 wherein means are provided for storing the first and second output signal before subtracting.

5. The invention of claim 1 wherein the means for producing a first and second output signal further includes a pair of chromatic filters for transmitting light rays of a respective first and second wavelength, means for intersecting the beam of light energy in a predetermined sequence and timing means for identifying the first output signal with a first chromatic filter and the second output signal with a second chromatic filter whereby subsequent signal processing can be accomplished.

6. The invention of claim 1 wherein the means for receiving a reflected portion of the beam includes a light splitting dichroic mirror for selectively transmitting light rays of a first wavelength and for reflecting light rays of a second wavelength, a first light receiving element for receiving the light rays transmitted through the dichroic mirror to produce the first output signal and a second light receiving element for receiving the light rays reflected off the dichroic mirror to produce the second output signal.

7. The invention of claim 6 wherein the first wavelength is longer than 600 nanometers and the second wavelength is shorter than 600 nanometers.

8. The invention of claim 1 wherein the means for producing a first output signal includes a neutral density filter for adjusting the intensity of the reflected first wavelength for balancing its reference level to coincide with the second wavelength output signal for subsequent processing.

9. An eye fundus plethysmograph assembly capable of measuring the amount of blood in blood vessels adjacent a human eye fundus without contacting or distorting the eye comprising;

a source of at least a first wavelength of light energy longer than 600 nanometers and a second wavelength of light energy shorter than 600 nanometers;

means for directing the first and second wavelengths of energy into a patients eye for reflection from the fundus, the eye being concurrently in a natural undisturbed configuration; means for receiving a reflected portion of the respective first and second wavelengths of light energy having a constant variation in intensity due to minute movements of the eye;

means for producing a first plethysmograph output signal representative of a measurement of the reflected first wavelength including the eye movement intensity variation output and a second output signal representative of the reflected second wavelength including the eye movement intensity variation; and compensation means for subtracting one of the first and second output signals from the other to provide a representative plethysmograph measurement output of the amount of blood in vessels adjacent the eye fundus, the measurement being free of any variation in intensity due to minute movements of the eye.

10. The invention of claim 9 wherein the means for receiving a reflected portion of the respective first and second wavelengths includes a light splitting dichroic mirror for selectively transmitting light rays of a first wavelength and for reflecting light rays of a second wavelength, a first light receiving element for receiving the light rays transmitted through the dichroic mirror to produce the first output signal and a second light receiving element for receiving the light rays reflected off the dichroic mirror to produce the second output signal.

11. The invention of claim 10 wherein the means for producing a first output signal includes a neutral density filter for adjusting the intensity of the reflected first wavelength for balancing its reference level to coincide with the second wavelength output signal for subsequent processing.

12. An eye fundus plethysmograph assembly capable of measuring the amount of blood in blood vessels adjacent a human eye fundus without contacting or distorting the eye over a cyclic period of time to provide an envelope of information comprising;

a source of at least a first wavelength of light energy and a second wavelength of light energy;

means for directing the first and second wavelengths of energy into a patients eye for reflection from the fundus, the eye being concurrently in a natural undisturbed configuration;

means for receiving a reflected portion of the respective first and second wavelengths of light energy having a constant variation in intensity due to minute movements of the eye;

means for producing a first plethysmograph output signal representative of a measurement of the reflected first wavelength and a second output signal representative of the reflected second wavelength including a pair of chromatic filters for transmitting light rays of a respective first and second wavelength, means for intersecting the beam of light energy in a predetermined sequence and timing means for identifying the first plethysmograph output signal with a first chromatic filter and the second output signal with a second chromatic filter whereby subsequent signal processing can be accomplished, and compensation means for subtracting one of the first and second output signals from the other to provide a representative measurement output of the amount of blood in vessels adjacent the eye fundus, the measurement being free of any variation in intensity due to minute movements of the eye.

13. An eye fundus plethysmograph assembly for obtaining, without contacting or distorting the eye, a plethysmogram in a wave form representative of change in the amount of blood in the eye fundus arterial blood vessels due to the pulsation from the heartbeat comprising:

light source means of standard light intensity;

means responsive to the change in intensity of light from the light source means reflected on the fundus and cornea of a subject eye for producing a first output signal varying in a waveform with respect to at least a first wavelength within a first wavelength band and a second output signal varying in a waveform with respect to at least a second wavelength within a second wavelength band other than the first wavelength band, the waveform of the first and second output signals differing from each other by the difference of intensity of light component reflected at the fundus caused by the difference of the wavelength;

means for subtracting one of the first and second output signals from the other to provide a third output signal representative of the difference between the first and second output signals caused by the difference of wavelength of light reflected at the fundus, wherein the third output signal, which contains an information of fundus reflection, also varies due to the pulsation from the heartbeat to form a desired plethysmogram with any influence of the intensity of cornea reflection light, which varies in response to the minute eyeball trembling, cancelled as a result of the wavelength insensitivity of the cornea reflection, and output means coupled to the subtraction means for producing a plethysmographic representation of the amount of blood in the eye fundus.

* * * * *